US008163518B2

(12) United States Patent
Arnott et al.

(10) Patent No.: US 8,163,518 B2
(45) Date of Patent: Apr. 24, 2012

(54) MICROWAVE ASSISTED DEGLYCOSYLATION OF PROTEINS FOR MOLECULAR WEIGHT DETERMINATION BY MASS SPECTROMETRY

(75) Inventors: David P. Arnott, San Mateo, CA (US); Jennie Lill, Pacifica, CA (US); Wendy N. Sandoval, San Francisco, CA (US); Richard L. Vandlen, Hillsborough, CA (US)

(73) Assignee: Genetech, Inc., South San Francisco, CA (US)

( * ) Notice: Subject to any disclaimer, the term of this patent is extended or adjusted under 35 U.S.C. 154(b) by 1147 days.

(21) Appl. No.: 11/741,490

(22) Filed: Apr. 27, 2007

(65) Prior Publication Data

US 2007/0259398 A1 Nov. 8, 2007

Related U.S. Application Data

(60) Provisional application No. 60/797,334, filed on May 2, 2006.

(51) Int. Cl.
*C12P 21/06* (2006.01)
*C12N 13/00* (2006.01)
(52) U.S. Cl. ................................. 435/68.1; 435/173.2
(58) Field of Classification Search ............... 435/68.1, 435/173.2
See application file for complete search history.

(56) References Cited

U.S. PATENT DOCUMENTS

| | | | | | |
|---|---|---|---|---|---|
| 5,350,686 | A | * | 9/1994 | Jhingan | 435/173.2 |
| 6,376,663 | B1 | * | 4/2002 | Williams et al. | 536/127 |
| 2002/0150969 | A1 | * | 10/2002 | Derkx et al. | 435/68.1 |
| 2002/0193573 | A1 | * | 12/2002 | Nock et al. | 530/388.1 |
| 2003/0059432 | A1 | * | 3/2003 | Dillon et al. | 424/146.1 |
| 2003/0232755 | A1 | * | 12/2003 | Williams et al. | 514/12 |
| 2004/0068101 | A1 | * | 4/2004 | Hsiung et al. | 530/409 |
| 2004/0072741 | A1 | * | 4/2004 | Jay | 514/12 |
| 2004/0185545 | A1 | * | 9/2004 | Simpson et al. | 435/183 |
| 2005/0232929 | A1 | * | 10/2005 | Kadkhodayan et al. | 424/178.1 |

OTHER PUBLICATIONS

Papac, DI et al. A high-throughput microscale method to release N-linked oligosaccharides from glycoproteins for matrix-assisted laser desorption/ionization time-of-flight mass spectrometric analysis. Glycobiology. 1998. 8(5): 445-454.*
Das Sk., "Application of Microwave Irradiation in the Synthesis of Carbohydrates" *Synlett* 6:915-932 (2004).
Hua at al., "Microwave-assisted specific chemical digestion for rapid protein identification" *Proteomics* 6:586-591 (2006).
Itonori at al., "Microwave-mediated analysis for sugar, fatty acid, and sphingoid compositions of glycosphingolipids" *J Lipid Res.* 45:574-581 (2004).
Kappe CO., "Controlled microwave heating in modern organic synthesis" *Angew Chem Int Ed.* 43:6250-6284 (2004).
Lee at al., "Characterization of oligosaccharide moieties of glycopeptides by microwave-assisted partial acid hydrolysis and mass spectrometry" *Rapid Commun Mass Spectrom.* 19:1545-1550 (2005).
Lee at al., "Characterization of oligosaccharide moieties of intact glycoproteins by microwave-assisted partial acid hydrolysis and mass spectrometry" *Rapid Commun Mass Spectrom.* 19:2629-2635 (2005).
Lin at al., "Microwave-assisted enzyme-catalyzed reactions in various solvent systems" *J Am Soc Mass Spectrom.* 16:581-588 (2005).
Mavandadi at al., "Microwave-assisted chemistry in drug discovery" *Curr Top Med Chem.* 4(7):773-792 (2004).
Palm at al., "A monolithic PNGase F enzyme microreactor enabling glycan mass mapping of glycoproteins by mass spectrometry" *Rapid Commun Mass Spectrom.* 19:1730-1738 (2005).
Pramanik at al., "Microwave-enhanced enzyme reaction for protein mapping by mass spectrometry: a new approach to protein digestion in minutes" *Protein Sci.* 11:2676-2687 (2002).
Sandoval at al., "Rapid removal of N-linked oligosaccharides using microwave assisted enzyme catalyzed deglycosylation" *International Journal of Mass Spectrometry* 259:117-123 (2007).
Zhong at al., "Microwave-assisted acid hydrolysis of proteins combined with liquid chromatography MALDI MS/MS for protein identification" *J Am Soc Mass Spectrom.* 16:471-481 (2005).
Fan et al., "A method for proteomic identification of membrane-bound proteins containing Asn-linked oligosaccharides" *Analytical Biochemistry* 332(1):178-186 (Sep. 1, 2004).
Fountoulakis et al., "Hydrolysis and amino acid composition analysis of proteins" *Journal of Chromatography* 826(2):109-134 (Nov. 27, 1998).
Harvey, David J., "Matrix-assisted laser desorption/ionization mass spectrometry of carbohydrates and glycoconjugates" *International Journal of Mass Spectrometry* 226:1-35 (2003).
Lill et al., "Microwave-assisted proteomics" *Mass Spectrometry Reviews* 26(5):657-671 (Sep. 2007).
Vesper et al., "Assessment of microwave-assisted enzymatic digestion by measuring glycated hemoglobin A1c by mass spectrometry" *Rapid Communications in Mass Spectrometry* 19(19):2865-2870 (2005).
Wuhrer et al., "Protein glycosylation analysis by liquid chromatography-mass spectrometry" *Journal of Chromatography B* 825(2):124-133 (Oct. 25, 2005).
Zhong et al., "Protein sequencing by mass analysis of polypeptide ladders after controlled protein hydrolysis" *Nature Biotechnology* 22(10):1291-1296 (Oct. 2004).

* cited by examiner

*Primary Examiner* — Allison Ford
*Assistant Examiner* — Susan E Fernandez
(74) *Attorney, Agent, or Firm* — Genentech, Inc.; Alex Andrus

(57) ABSTRACT

Methods are presented for microwave assisted, enzymatic deglycosylation of proteins. The rate at which deglycosylation is achieved and without protein degradation facilitates rapid and accurate molecular weight determination by mass spectrometry.

18 Claims, 12 Drawing Sheets

MICROWAVE ASSISTED DEGLYCOSYLATION OF PROTEINS FOR MOLECULAR WEIGHT DETERMINATION BY MASS SPECTROMETRY

This non-provisional application filed under 37 CFR §1.53 (b) claims the benefit under 35 USC §119(e) of U.S. Provisional Application Ser. No. 60/797,334 filed on 2 May 2006, which is incorporated by reference in its entirety.

FIELD OF THE INVENTION

The invention relates to methods for removing carbohydrate groups from proteins under mild, microwave conditions. The methods facilitate accurate molecular weight determination and analysis by mass spectrometry.

BACKGROUND OF THE INVENTION

The vast microheterogeneity of the eukaryotic proteome is due to several genetic and proteomic events including; genome splice variation, intracellular processing and the dynamic process of post-translational modification (PTM). Glycosylation stands as one of the most common, yet complex, post-translational modifications. Glycoproteins, i.e. glycosylated proteins, are involved in a wide range of biological functions such as receptor binding, cell signaling, immune recognition, inflammation and pathogenicity. The glycosylation and deglycosylation process in vivo plays an important role in key proteomic functions such as protein folding, protein and cellular trafficking, protein stabilization, protease protection and quaternary structure (R. A. Dwek. (1998) Biological importance of glycosylation. Dev. Biol. Stand. 96:43-7). Glycosylation can also have profound effects on receptor binding and inflammation, indeed, the onset or recovery from many diseases has been linked to the presence, diversity or lack of glycosylation sites, for example HIV-2 (Shi et al. (2005) J. Gen. Virol. 86:3385-96), Creutzfeldt-Jakob disease—CJD (Silveyra, et al (2005) J. Neurochem. online), rheumatoid arthritis (Gindzienska-Sieskiewicz et al. (2005) Postepy Hig. Med. Dosw. 59:485-9) and tuberculosis (Romain et al (1999) Infect. Immun. 67:5567-72).

Glycosylation sites are classified as either N-linked (via the amide nitrogen of asparagine) or O-linked (via the hydroxyl groups of serine, threonine and occasionally hydroxylysine or hydroxyproline). Due to the diverse nature of carbohydrate structures, characterization of glycoproteins has proven challenging. Since glycosylation is complex and heterogeneous, mapping the glycome can be an extremely challenging task. Pin-pointing glycosylation sites has been performed in a number of ways including glycol-enrichment using lectin affinity resins (Yang et al (2005) Proteomics. 5:3353-66), beta elimination followed by Michael addition with either a tag or an affinity group to flag or affinity purify peptides containing O-linked sugar residues (Rademaker et al (1998) Anal. Biochem. 257:149-60), utilization of chemoenzymatic properties by engineering the galactostransferase enzyme to selectively label O-GlcNAc proteins with a ketone-biotin tag followed by affinity selection (Khidekel et al (2004) Proc. Natl. Acad. Sci. U.S.A. 101:13132-7) and comparative chromatographic mapping/profiling of the enzymatic cleavage products of a protein before and after deglycosylation followed by mass spectrometric analysis.

For a chromatographic mapping protocol, and for other analytical scenarios, complete deglycosylation of both proteins and peptides is often desirable. For example, deglycosylation may reduce smearing during protein separation by sodium dodecyl sulphate polyacrylamide gel electrophoresis (SDS-PAGE) or may allow easier ionization and spectral interpretation during mass spectrometric analysis. This may be particularly useful when looking at intact molecular weights of proteins that may be skewed due to heterogeneity from an abundance of PTM's. For example, the majority of naturally expressed and recombinant antibodies produced in eukaryotic cell lines have N-linked glycosylated heavy chains. In the case of therapeutic antibodies, deglycosylation is often necessary in characterizing modifications such as the presence of C-terminal lysines, or for labelled or drug-conjugated monoclonal antibodies (A. M. Wu & P. D. Senter. (2005) Nature Biotechnology 23:1137-46), to monitor the number of small molecules coupled to the immunoglobulin. For these and a plethora of other reasons, it is often advantageous to deglycosylate glycoproteins.

The two conventional methods for the deglycosylation of O-linked sugars are: (i) beta elimination, most typically followed with Michael addition using a thiol for stabilization, and (ii) treatment of the protein with the enzyme sialidase. Many proteins are heterogeneously glycosylated with a mixture of both O- and N-linked sugars.

Over the past decade, several techniques have described improvements upon traditional overnight incubation of glycoproteins with their respective deglycosylating enzymes/chemicals. These include; optimization of a chemical procedure using anhydrous trifluoromethane sulfonic acid—TFMSA to cleave all sugar residues from the glycol-protein (T. S. Raju. & E. A. Davidson. (1994) Biochem. Mol. Biol. Int. 34: 943-54), PVDF-immobilization strategies of a glycosylated protein of interest followed by incubation with a deglycosylating enzyme (Papac et al (1998) Glycobiology 8:445-454), on-chip deglycosylation using SELDI hydrophobic and hydrophilic chip technology (Ge et al (2005) Anal. Chem. 77:3644-3650), incubation of glycoproteins with PNGase F in the presence of enzyme-friendly surfactants (Yu et al (2005) Rapid communications in Mass Spectrometry 19:2331-2336), and engineering of hybrid de-glycosylation enzymes for facile immobilization on cellulose (Kwan et al (2005) Protein Engineering, Design & Selection, 497-501).

In addition to in-solution or membrane immobilized deglycosylation techniques, in-gel deglycosylation has been described whereby O-glycosylated proteins of up to 150 KDa can be deglycosylated and extracted for analysis. Complete deglycosylation of standard glycoproteins such as Fetuin and RNase B requires 2 hours (Kilz et al (2002) Journal of Mass spectrometry 37:331-335). Deglycosylation protocols using PNGase F typically requires up to 24 hours to complete using conventional protocols, i.e. convection or conduction heating in water baths. In many laboratories, e.g. high-throughput commercial settings, a complete deglycosylation strategy in a short amount of time would be extremely advantageous.

For many types of chemical reactions, microwave energy provides a useful method of heating (Shipe et al (2005) Drug Discovery Today: Technologies 2(2):155-161; "Scale-up of microwave-assisted organic synthesis" Roberts, Brett A.; Strauss, Christopher R. pp. 237-271, Editor(s): Tierney, Jason P.; Lindstroem, Pelle. in *Microwave Assisted Organic Synthesis* (2005), Blackwell Publishing Ltd., Oxford, UK; Kappe, C. Oliver (2004) Angewandte Chemie, International Edition, 43(46):6250-6284; Das, S. (2004) Synlett (6):915-932; Mavandadi, F., Lidstroem, P. (2004) Current Topics in Medicinal Chemistry 4(7):773-792). Microwaves are generally categorized as having frequencies within the electromagnetic spectrum of between about 1 gigahertz and 1 terahertz, and corresponding wavelengths of between about 1 millimeter and 1 meter. Microwaves tend to react well with polar molecules and cause them to rotate. This in turn tends to heat the material under the influence of the microwaves. In many circumstances, microwave heating is quite advantageous because microwave radiation tends to interact immediately with substances that are microwave-responsive, thus raising the temperature very quickly. Other heating methods, including conduction or convection heating, are advantageous in certain circumstances, but generally require longer lead times to heat any given material.

In a similar manner, the cessation of application of microwaves causes an immediate corresponding cessation of the molecular movement that they cause. Thus, using microwave radiation to heat chemicals and compositions can offer significant advantages for initiating, controlling, and accelerating certain chemical and physical processes. Microwave radiation technology has been introduced into the proteomics arena, allowing faster alternatives to traditional methods for amino acid protein hydrolysis (S. H. Chiou, & K. T. Wang. (1990) *Current Research in protein chemistry*, Academic Press Inc.), tryptic digestion (Pramanik et al (2002) Protein Science. 11:2676-2687; Lin et al (2005) Jour. Amer. Soc. Mass Spec. 16:581-588) and microwave acid-assisted hydrolysis—MAAH (Zhong, et al (2004) Nature Biotechnology 22:1291-6; Zhong et al (2005). Jour. Amer. Soc. Mass Spec. 16:471-81; Hua et al (2005) Proteomics (online). MAAH was recently demonstrated for characterizing oligosaccharide moieties of glycopeptides using partial acid hydrolysis with trifluoroacetic acid (Lee et al (2005) Rapid Commun. Mass spectrum 19:1545-50; Lee et al (2005) Rapid Commun. Mass spectrum 19:2629-2635).

Recent advances in protein analysis by mass spectrometry (MS) are due to front-end gas phase ionization and introduction techniques such as electrospray ionization (ESI), matrix-assisted laser desorption ionization (MALDI, US 2003/0027216) and Surface Enhanced Laser Desorption Ionization (SELDI, U.S. Pat. No. 6,020,208), as well as improvements in instrument sensitivity, resolution, mass accuracy, bioinformatics, and software data deconvolution algorithms ("Electrospray Ionization Mass Spectrometry: Fundamentals, Instrumentation, and Applications", Cole, R. B., Ed. (1997) Wiley, New York; "Modern Protein Chemistry Practical Aspects", Howard, G. C. and Brown, W. E., Eds. (2002) CRC Press, Boca Raton, Fla., p. 71-102).

Antibody therapy has been established for the targeted treatment and diagnosis of patients with cancer, immunological and angiogenic disorders. The aim of antibody therapy and diagnosis is to exploit the combination of high specificity and affinity of the antibody-antigen interaction, to enable detection and/or treatment of a particular lesion or disorder. The antibody is used alone, or is conjugated, i.e. loaded, with another moiety such as a detection label, pharmacokinetic modifier, radioisotope, toxin, or drug. The use of antibody-drug conjugates (ADC), i.e. immunoconjugates, for the local delivery of cytotoxic or cytostatic agents to kill or inhibit tumor cells in the treatment of cancer (Syrigos and Epenetos (1999) Anticancer Research 19:605-614; Niculescu-Duvaz and Springer (1997) Adv. Drug Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al. (1986) Lancet pp. (Mar. 15, 1986):603-05; Thorpe, (1985) "Antibody Carriers Of Cytotoxic Agents In Cancer Therapy: A Review," in *Monoclonal Antibodies '84: Biological And Clinical Applications*, A. Pinchera et al. (eds), pp. 475-506). Maximal efficacy with minimal toxicity is sought thereby. Efforts to design and refine ADC have focused on the selectivity of monoclonal antibodies (MAbs) as well as drug-linking and drug-releasing properties. Both polyclonal antibodies and monoclonal antibodies linked to drugs including daunomycin, doxorubicin, methotrexate, and vindesine have been reported as useful in these strategies (Rowland et al., (1986) Cancer Immunol. Immunother., 21:183-87). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins and drugs may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

The above-mentioned antibody-drug conjugates (ADC) which are approved or under development for therapeutic use are heterogeneous mixtures where the process of covalent attachment of the drug moiety to the antibody is largely uncontrolled and the resulting conjugation products are incompletely characterized. In addition, the drug loading (drug/Ab ratio) is a statistical average of the collection of ADC molecules in a composition or formulation. Because of the heterogeneous nature of antibody-drug conjugate compositions, pharmacokinetic samples collected from biological sources after administration are difficult to evaluate. ELISA assays are limited to detection of antibody-antigen binding (DiJoseph et al (2004) Blood 103:1807-1814). UV spectroscopy can measure the total absorbance of certain fluorescent or UV-active drug moieties or metabolites, but cannot distinguish between free drug and antibody-drug conjugate. Methods to facilitate characterization of antibodies and antibody conjugates are useful for therapeutic development.

SUMMARY OF THE INVENTION

The invention provides methods of deglycosylation of proteins comprising treating a glycosylated protein with an enzyme under microwave conditions whereby a deglycosylated protein is formed.

In certain embodiments, the deglycosylated protein may be applied to a desalting media, eluted, and analyzed by mass spectrometry.

In one aspect, the invention relates to a rapid procedure for the removal of N-linked glycosylation sites on proteins using microwave technology. Using N-glycosidase F (PNGase F) for removal of N-linked sugar residues, complete deglycosylation is achieved on a range of proteins, including antibodies, in less than about one hour (Sandoval et al (2007) Intl. Jour. Mass Spec. (259(1-3):117-123).

The invention provides methods for rapid deglycosylation of N-linked proteins. The invention includes methods under microwave conditions to effect complete deglycosylation in about 5 minutes to one hour, with partial deglycosylation occurring in less than 60 seconds.

In another aspect, the invention includes methods of analyzing a sugar moiety removed from the glycosylated protein under microwave conditions, wherein the sugar moiety is analyzed by mass spectrometry. The sugar moiety may be isolated by high pH anion-exchange chromatography.

DETAILED DESCRIPTION OF EXEMPLARY EMBODIMENTS

Figure 1A:
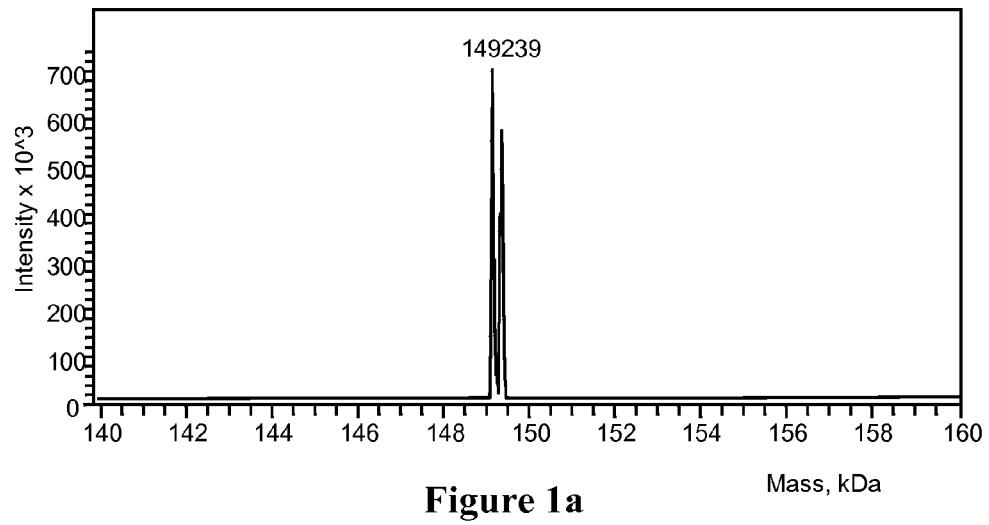
FIG. 1a shows a deconvoluted mass spectra of intact, non-reduced glycosylated bevacizumab (AVASTIN®, Genentech, South San Francisco Calif.).

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

DEFINITIONS

Unless stated otherwise, the following terms and phrases as used herein are intended to have the following meanings:

The term "glycome" means the collective identity of the entirety of carbohydrates in a cell or in an organism.

The terms "sugar", "glycan", "polysaccharide", "oligosaccharide", and "carbohydrate" are used interchangeably herein. Carbohydrates are chemical compounds that comprise oxygen, hydrogen, and carbon atoms. They consist of monosaccharide sugars of varying chain lengths and that have the general chemical formula $C_n(H_2O)_n$ or are derivatives of such.

The term "glycosylation" means the process or result of addition of saccharides to proteins and lipids. The process is one of four principal co-translational and post-translational modification steps in the synthesis of membrane and secreted proteins and the majority of proteins synthesized in the rough endoplasmic reticulum undergo glycosylation. It is an enzyme-directed site-specific process, as opposed to the non-enzymatic chemical reaction of glycation. N-linked glycosylation may occur at the amide nitrogen of asparagine side chains and O-linked glycosylation may occur at the hydroxy oxygen of serine and threonine side chains.

"Microwave" is the term generally used to describe the portion of the electromagnetic spectrum that has wavelengths (lambda) between the far infrared and the radio frequency; i.e. between about one millimeter and about 30 centimeters, with corresponding frequencies in the range from about 1 to 100 gigahertz (GHz). Energy in the form of microwaves can be transferred to substances that are present in the beam line of the microwave radiation. Absorption of the energy occurs when dipolar molecules rotate to align themselves with the fluctuating electric field component of the irradiation or when ions move back and forth by the same phenomena, generating heat (Mavandadi, F., Lidstroem, P. (2004) Current Topics in Medicinal Chemistry 4(7):773-792). The amount of heat generated by a given reaction mixture is a complex function of its dielectric property, volume, geometry, concentration, viscosity and temperature (Galema, S. A. (1997) Chem. Soc. Rev. 26:233-238). In a microwave reactor, microwaves are generated by a magnetron and led into the reaction chamber, the cavity, through a wave-guide. Commercial microwave reactors for research laboratory use are available and capable of reliably heating a variety of mixtures, with variable and precise power, time and temperature control.

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species.

An antibody is a protein generated by the immune system that is capable of recognizing and binding to a specific antigen. (Janeway, et al. (2001) "Immunobiology", 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', $F(ab')_2$, and Fv fragments; diabodies; linear antibodies; fragments produced by a Fab expression library, anti-idiotypic (anti-Id) antibodies, CDR (complementary determining region), ECD (extracellular domain), and epitope-binding fragments of any of the above which immunospecifically bind to cancer cell antigens, viral antigens or microbial antigens, single-chain antibody molecules; and multispecific antibodies formed from antibody fragments.

An "intact antibody" herein is one comprising a VL and VH domains, as well as complete light and heavy chain constant domains.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (U.S. Pat. No. 4,816,567). The "monoclonal antibodies" may also be isolated from phage antibody libraries using the techniques described in Clackson et al (1991) Nature, 352: 624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape etc) and human constant region sequences.

"Antibody fragments" comprise a portion of an intact antibody, e.g. comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragment(s).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\varepsilon$, $\gamma$, and $\mu$ respectively. The subunit structures and three-dimensional configurations of different classes of immunoglobulins are well known.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native antibody or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (MAb) to an antigen-of-interest can be prepared by using any technique known in the art which provides for the production of antibody molecules by continuous cell lines in culture. These include, but are not limited to, the hybridoma technique originally described by Köhler and Milstein (1975) Nature 256: 495-497), the human B cell hybridoma technique (Kozbor et al (1983) Immunology Today 4:72), and the EBV-hybridoma technique (Cole et al (1985) in *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the MAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al (1983) Proc. Natl. Acad. Sci. U.S.A. 80:7308-7312; Kozbor et al (1983) Immunology Today 4:72-79; and Olsson et al (1982) Methods in Enzymology 92:3-16).

The antibody can also be a bispecific antibody. Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al (1986) Methods in Enzymology, 121:210; Rodrigues et al (1993) J. of Immunology 151:6954-6961; Carter et al (1992) Bio/Technology 10:163-167; Carter et al (1995) J. of Hematotherapy 4:463-470; Merchant et al (1998) Nature Biotechnology 16:677-681. Methods for making bispecific antibodies are known in the art (Milstein et al (1983) Nature 305:537-539; WO 93/08829; Traunecker et al (1991) EMBO J. 10:3655-3659.

Using such techniques, bispecific antibodies can be prepared for conjugation as ADC in the treatment or prevention of disease as defined herein.

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, $C_H2$, and $C_H3$ regions. The first heavy-chain constant region ($C_H1$) may contain the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Hybrid or bifunctional antibodies can be derived either biologically, i.e., by cell fusion techniques, or chemically, especially with cross-linking agents or disulfide-bridge forming reagents, and may comprise whole antibodies or fragments thereof (EP 105360; WO 83/03679; EP 217577).

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, for e.g., Kabat et al, (1991) in *Sequences of Proteins of Immunological Interest*, Fifth Edition, National Institute of Health, Bethesda, Md.; Kabat et al (1980) J. of Immunology 125(3): 961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird (1988) Science 242:423-42; Huston et al., (1988) Proc. Natl. Acad. Sci. USA 85:5879-5883; and Ward et al (1989) Nature 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions (U.S. Pat. No. 4,816,567; and U.S. Pat. No. 4,816,397, which are incorporated herein by reference in their entirety.) Chimeric and humanized monoclonal antibodies can be produced by recombinant DNA techniques known in the art, for example using methods described in WO 87/02671; EP 184,187; EP 171496; EP 173494; WO 86/01533; U.S. Pat. No. 4,816,567; EP 12023; Berter et al (1988) Science 240:1041-1043; Liu et al (1987) Proc. Natl. Acad. Sci. USA 84:3439-3443; Liu et al (1987) J. Immunol. 139:3521-3526; Sun et al (1987) Proc. Natl. Acad. Sci. USA 84:214-218; Nishimura et al (1987) Cancer. Res. 47:999-1005; Wood et al (1985) Nature 314: 446-449; and Shaw et al (1988) J. Natl. Cancer Inst. 80:1553-1559 Morrison (1985) Science 229:1202-1207; Oi et al (1986) BioTechniques 4:214; U.S. Pat. No. 5,225,539; Jones et al (1986) Nature 321:552-525; Verhoeyan et al (1988) Science 239:1534; and Beidler et al (1988) J. Immunol. 141: 4053-4060; each of which is incorporated herein by reference in its entirety.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995) Int. Rev. Immunol. 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al (1994) Biotechnology 12:899-903). Human antibodies can also be produced using various techniques known in the art, including phage display libraries (Hoogenboom and Winter, J. Mol. Biol. 227:381 (1991); Marks et al (1991) J. Mol. Biol. 222:581).

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The term "receptor" includes any peptide, protein, glycoprotein (glycosylated protein), polycarbohydrate, or lipid that is uniquely expressed or overexpressed on the surface of a cell, and is exposed on the surface of a cell in a manner that will allow interaction with a circulating targeting agent, such as an antibody-drug conjugate. Cells bearing receptors include tumor cells.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

"Reactive functional groups" include, but are not limited to, olefins, acetylenes, alcohols, phenols, ethers, oxides, halides, aldehydes, ketones, carboxylic acids, esters, carbonates, amides, cyanates, isocyanates, thiocyanates, isothiocyanates, amines, hydrazines, hydrazones, hydrazides, diazo, diazonium, nitro, nitriles, mercaptans (thiols), sulfides, disulfides, sulfoxides, sulfones, sulfonic acids, sulfinic acids, acetals, ketals, anhydrides, sulfates, sulfenic acids, isonitriles, amidines, imides, imidates, nitrones, hydroxylamines, oximes, hydroxamic acids, thiohydroxamic acids, allenes, orthoesters, sulfites, enamines, ynamines, ureas, pseudoureas, semicarbazides, carbodiimides, carbamates, imines, azides, azo compounds, azoxy compounds, and nitroso compounds. Exemplary reactive functional groups include N-hydroxysuccinimide (NHS)esters, para-nitrophenyl (PNP) carbonates, pentafluorophenyl (PFP) carbonates, and maleimides. See: Sandler and Karo, Eds. in *Organic Functional Group Preparations*, Academic Press, San Diego, 1989.

"Linker", "Linker Unit", or "link" means a chemical moiety comprising a covalent bond or a chain of atoms that covalently attaches an antibody to a drug moiety. In various embodiments, a linker is specified as L. Linkers include a divalent radical such as an alkylene, an aryldiyl, a heteroaryldiyl, moieties such as: —$(CR_2)_nO(CR_2)_n$—, repeating units of alkyloxy (e.g. polyethylenoxy, PEG, polymethyleneoxy) and alkylamino (e.g. polyethyleneamino, Jeffamine™); and diacid ester and amides including succinate, succinamide, diglycolate, malonate, and caproamide.

Exemplary linker abbreviations include: MC=6-maleimidocaproyl, MP=maleimidopropanoyl, val-cit=valine-citrulline, dipeptide site in protease-cleavable linker, ala-phe=alanine-phenylalanine, dipeptide site in protease-cleavable linker, PAB=p-aminobenzyloxycarbonyl ("self immolative" portion of linker), SPP=N-Succinimidyl 4-(2-pyridylthio)pentanoate, SMCC=N-Succinimidyl 4-(N-maleimidomethyl)cyclohexane-1 carboxylate, SIAB=N-Succinimidyl (4-iodo-acetyl)aminobenzoate Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCl is 1-(3-dimethylaminopropyl)-3-ethylcarbodiimide hydrochloride, EDTA is ethylenediaminetetraacetic acid, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, LC/MS is liquid chromatography and mass spectrometry, MAAH is microwave assisted acid hydrolysis, MeOH is methanol, MQ is Milli-Q water, Mtr is 4-anisyldiphenylmethyl (or 4-methoxytrityl), nor is (1S,2R)-(+)-norephedrine, PBS is phosphate-buffered saline (Ph 7.4), PEG is polyethylene glycol, Ph is phenyl, PNGase F is N-glycosidase F, first isolated from *Flavobacterium meningosepticum*, PNGase A is N-glycosidase isolated from almonds, Pnp is p-nitrophenyl, PTM is post-translational modification, PVDF is polyvinylidene fluoride, PyBrop is bromo tris-pyrrolidino phosphonium hexafluorophosphate, SDS-PAGE is sodium dodecyl sulphate-polyacrylamide gel electrophoresis, SEC is size-exclusion chromatography, Su is succinimide, TFA is trifluoroacetic acid, TFMSA is trifluoromethane sulfonic acid, TLC is thin layer chromatography, TOF is time of flight, UV is ultraviolet, and val is valine.

Microwave-Assisted Deglycosylation of Proteins

Removal of the carbohydrate groups from a glycoprotein (glycosylated protein) prior to protein identification is usually preferred. Researchers often require deglycosylation to facilitate accurate molecular weight determination of antibodies to assess the presence of additional C-terminal lysines, to map a residue of modification and to assess the level of derivatization with a drug-conjugate, i.e. establish the average drug to antibody ratio. PNGase F is often an effective enzyme for the release of N-linked glycans from glycoproteins, in gel or in solution. However, proteolytic digestion of the native glycoprotein is often incomplete due to steric hindrance by the oligosaccharides. The methods of the invention may be conducted with PNGase of any type, including native or recombinant, and including PNGase F and PNGase A. The methods of the invention may be conducted with a catalytic amount of PNGase relative to substrate glycosylated protein. The molar ratio of PNGase to glycosylated protein may be between 1:10 to 1:1000.

Deglycosylation of proteins may be conducted in solution or in the gel slice after electrophoresis. The in-gel method includes the steps of: after gel electrophoresis, the glycosylated protein of interest is excised as a gel slice and destained in a destaining solution. The gel slice with the extracted protein is typically dried, resuspended in a PNGase F solution, and microwaved by the methods of the invention. The glycan-containing supernatant is removed and discarded. The gel slice containing the deglycosylated protein is washed and dried. Deglycosylated protein is eluted from the gel slice or digested in-gel, e.g. trypsin.

The invention generally includes methods of increasing the rate of chemical reactions while controlling an elevated temperature by applying sufficient microwave radiation to a temperature-monitored mixture of reagents including a glycosylated protein and an enzyme, with at least one of the reagents being thermally responsive to electromagnetic radiation in the microwave range.

Mass Spectrometry of Deglycosylated Proteins

Mass spectrometry is widely used for rapid identification of proteins by mass, i.e. molecular weight. Glycopeptides are often poorly ionized and signal suppressed relative to their deglycosylated forms due to the microheterogeneity of the attached glycans. Samples of incompletely deglycoslyated proteins are relatively more complicated to deconvolute their mass spectra. The measured mass of a protein is the average mass and the peak envelope extends over many individual masses. For example, a protein with a mass of 10 kDa. will have a peak envelope that is approximately 20 mass units wide (counting all isotope containing peaks with intensities greater than 1% of the most abundant peak (Anal. Chem. (1983) 55:353-356). In many types of mass spectrometry analysis, e.g. MALDI-TOF, spectra of glycosylated proteins exhibit peaks which are too wide at higher mass ranges to obtain enough resolution for accurate detection (Evershed et al. (2005) Rapid Commun. in Mass Spec. 7(10):882-886). The width of peaks reflects the isotope envelope and instrument resolution. For other mass spectrometry techniques, e.g. Q-TOF-MS or triple quad analyses, complex data from glycoproteins may be troublesome to deconvolute and obtain accurate mass determinations.

Microwave assisted deglycosylation of antibodies was performed in the presence of a catalytic amount of PNGase F at a range of temperatures from 37° C. to 60° C., and at various time points from 2 to 60 min, with and without reduction. After deglycosylation, the intact masses of the samples were analyzed by Q-TOF or triple-quadrupole mass spectrometry with the complex highly charged data being deconvoluted using the MaxEnt® (Waters Corp.) or ProMass Deconvolution™ (Novatia, LLC) programs respectively.

Figure 1B:
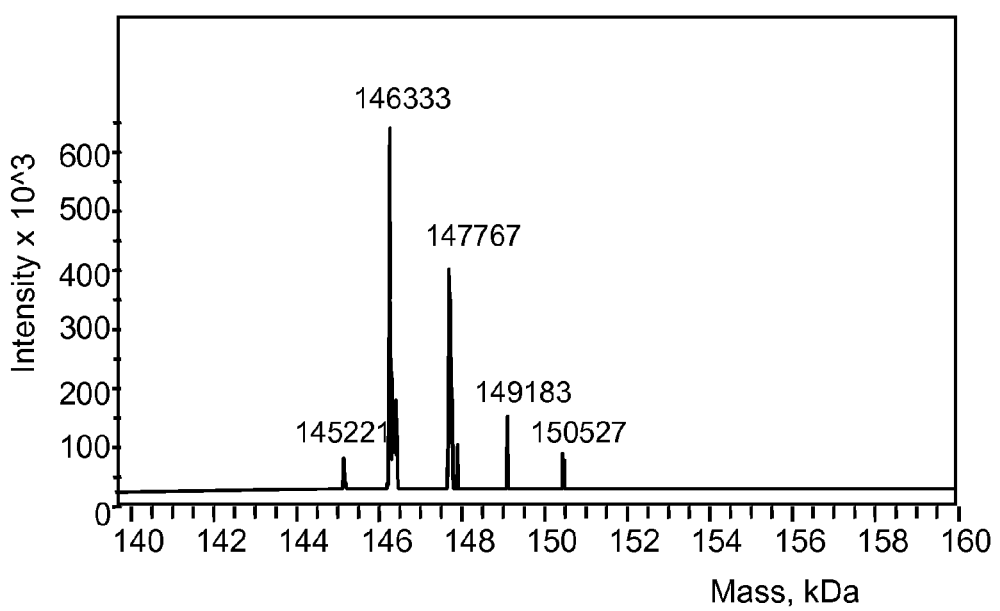
FIG. 1b shows a deconvoluted mass spectra of intact, non-reduced glycosylated bevacizumab and PNGase F after 5 minutes of microwave irradiation at 37° C.
Figure 1C:
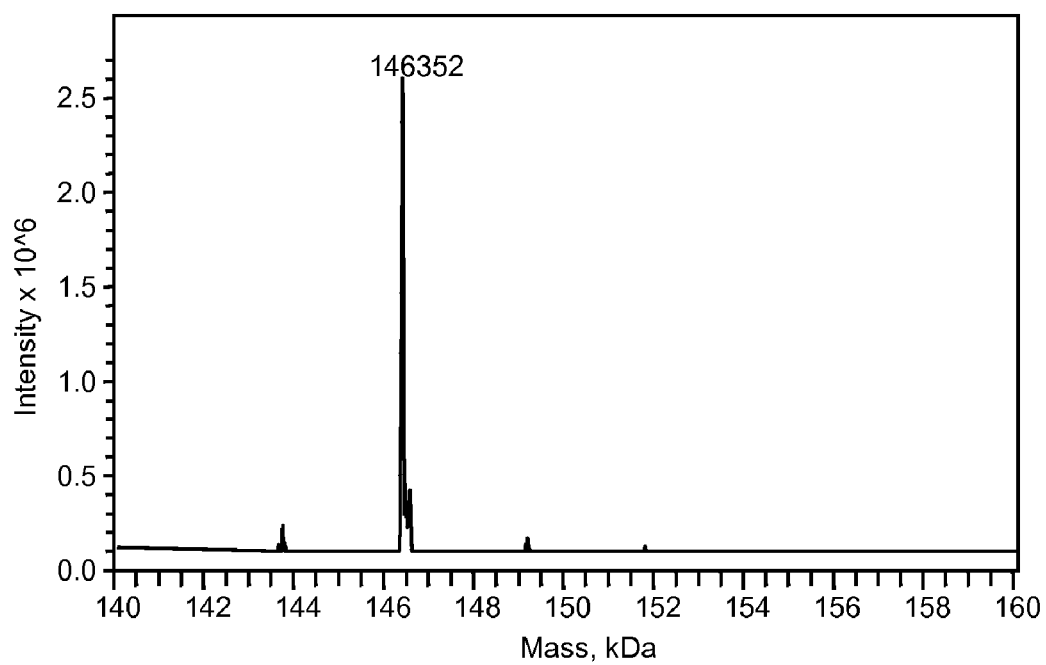
FIG. 1c shows a deconvoluted mass spectra of intact, non-reduced glycosylated bevacizumab and PNGase F after 10 minutes of microwave irradiation at 37° C.
Figure 2A:
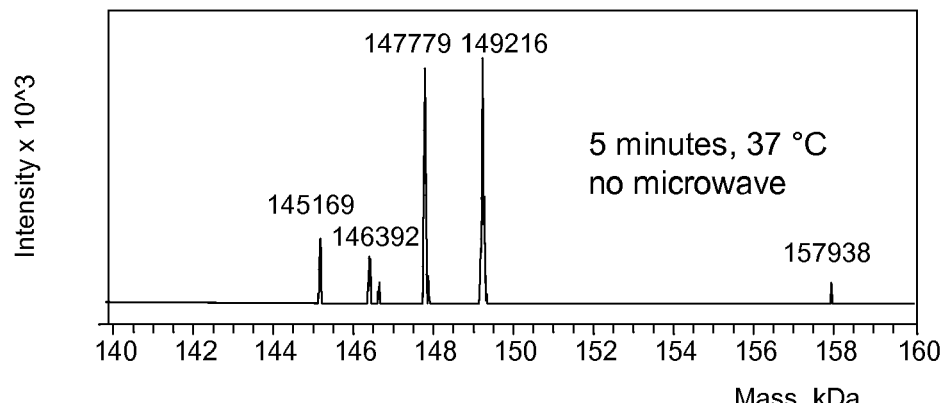
FIG. 2a shows a deconvoluted mass spectra of intact, non-reduced glycosylated bevacizumab and PNGase F (enzyme: substrate/1:10) after 5 minutes in a water bath, without microwave irradiation, at 37° C.
Figure 2B:
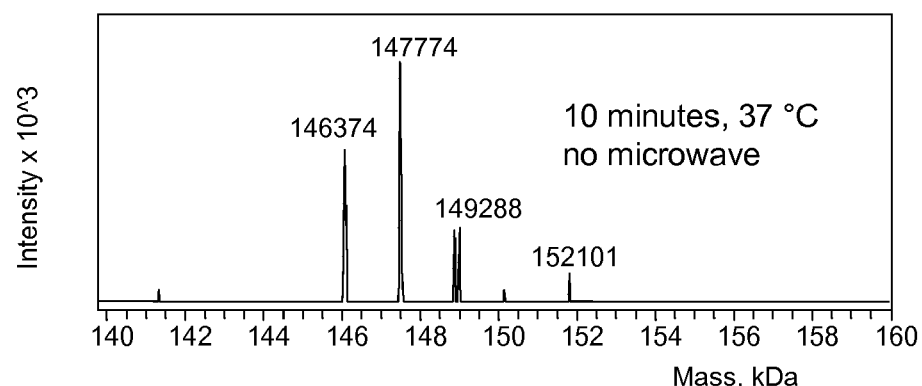
FIG. 2b a shows a deconvoluted mass spectra of intact, non-reduced glycosylated bevacizumab and PNGase F (enzyme: substrate/1:10) after 10 minutes in a water bath, without microwave irradiation, at 37° C.
Figure 2C:
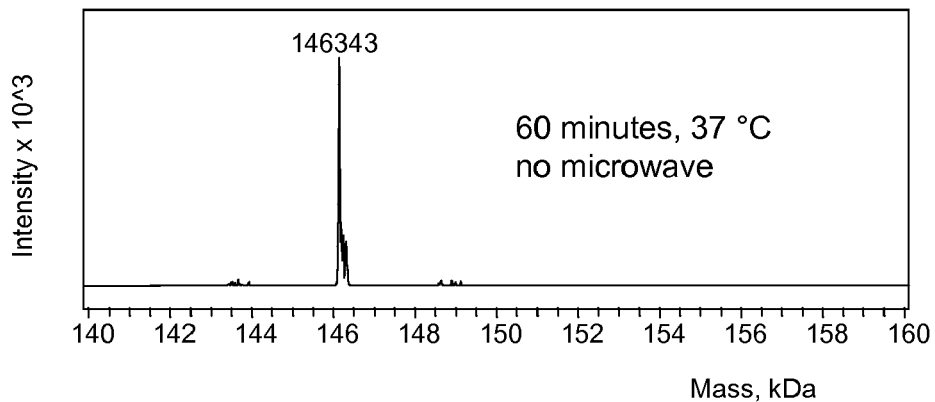
FIG. 2c shows a deconvoluted mass spectra of intact, non-reduced glycosylated bevacizumab and PNGase F (enzyme: substrate/1:10) after 60 minutes in a water bath, without microwave irradiation, at 37° C.

FIG. 1a shows the spectrum of the intact antibody bevacizumab (AVASTIN®, Genentech, Inc., South San Francisco, Calif.) prior to reduction with dithiothreitol (DTT). The starting antibody bevacizumab contains two carbohydrate additions of 1445 Da each, representing a 2100 G1-GalGlcNAc residue on each heavy chain (main peak at 149183 Da [M+H+2890]$^+$). After 5 minutes treatment with PNGase F and microwave irradiation at 37° C., the loss of one (147767 Da [M+H+1445]$^+$) and two (146333 Da [M+H]$^+$) sugars can be observed in FIG. 1b. After 10 min in the microwave, deglycosylation is complete (FIG. 1c). Acceleration of deglycosylation by microwave irradiation can be seen when the same mixture containing bevacizumab and PNGase F reaction was left to react at 37° C. without microwave irradiation (FIGS. 2a-c). Samples of aliquots from the mixture at time points of 5 minutes (FIG. 2a), 10 minutes (FIG. 2b), and 60 minutes (FIG. 2c) were analyzed by mass spectrometry. It can be observed that deglycosylation with microwave irradiation after 10 minutes (FIG. 1c) is farther advanced, and virtually complete, than deglycosylation without microwave irradiation after 10 minutes (FIG. 2b). Comparatively, complete deglycosylation of the antibody in a water bath at the same temperature was seen after incubation for 1 h (FIG. 1g).

Prior to deglycosylation, the heavy and light chains of antibodies may be separated by reductive cleavage of cysteine disulfide residues. Bevacizumab (10 μg, AVASTIN®, Genentech, South San Francisco, Calif.) was treated with 50 mM DTT in 0.1M Tris-HCl before deglycosylation.

Figure 3A:
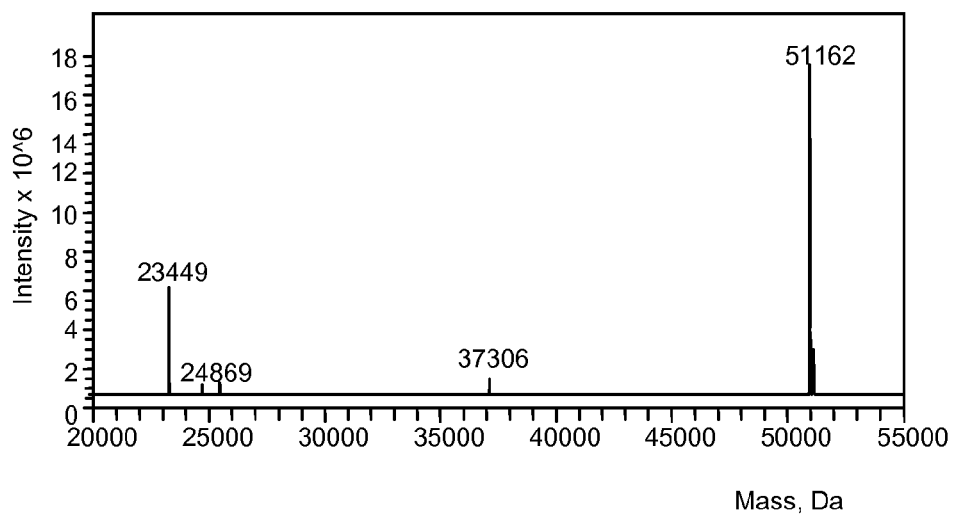
FIG. 3a shows a deconvoluted mass spectra of bevacizumab heavy chain after reduction with DTT.
Figure 3B:
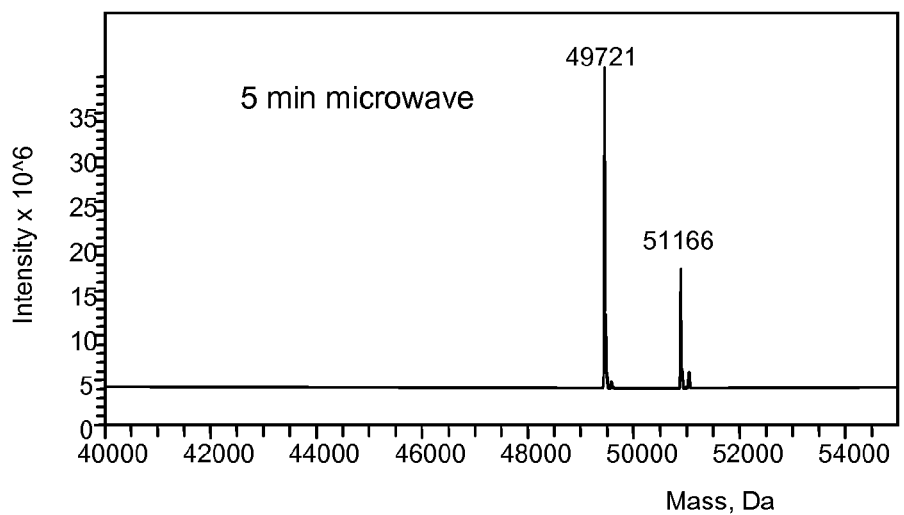
FIG. 3b shows a deconvoluted mass spectra of reduced bevacizumab heavy chain and PNGase F after 5 minutes of microwave irradiation at 37° C.
Figure 3C:
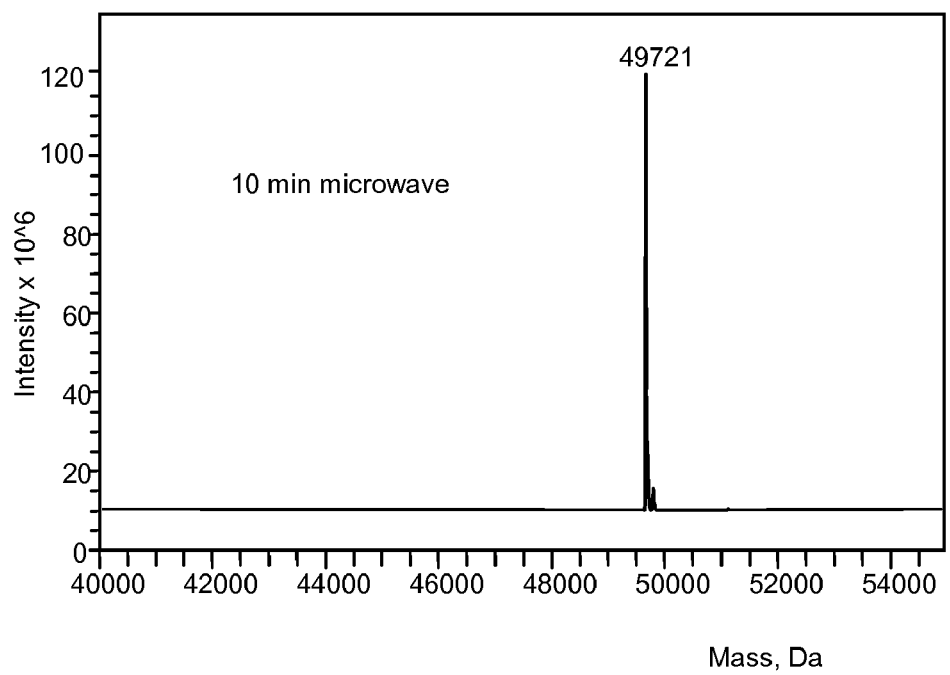
FIG. 3c shows a deconvoluted mass spectra of reduced bevacizumab heavy chain and PNGase F after 10 minutes of microwave irradiation at 37° C.
Figure 4A:
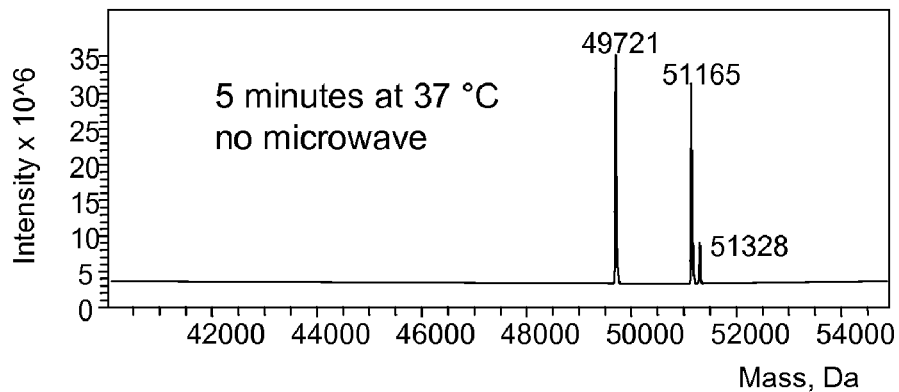
FIG. 4a shows a deconvoluted mass spectra of reduced bevacizumab heavy chain and PNGase F after 5 minutes in a water bath, without microwave irradiation, at 37° C.
Figure 4B:
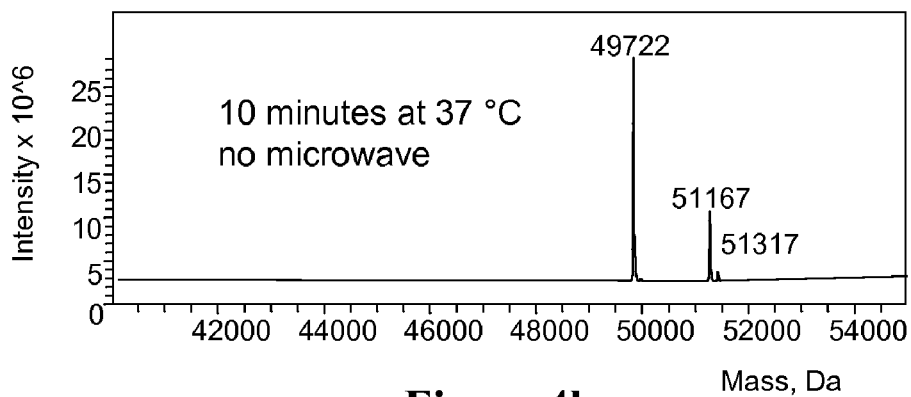
FIG. 4b a shows a deconvoluted mass spectra of reduced bevacizumab heavy chain and PNGase F after 10 minutes in a water bath, without microwave irradiation, at 37° C.
Figure 4C:
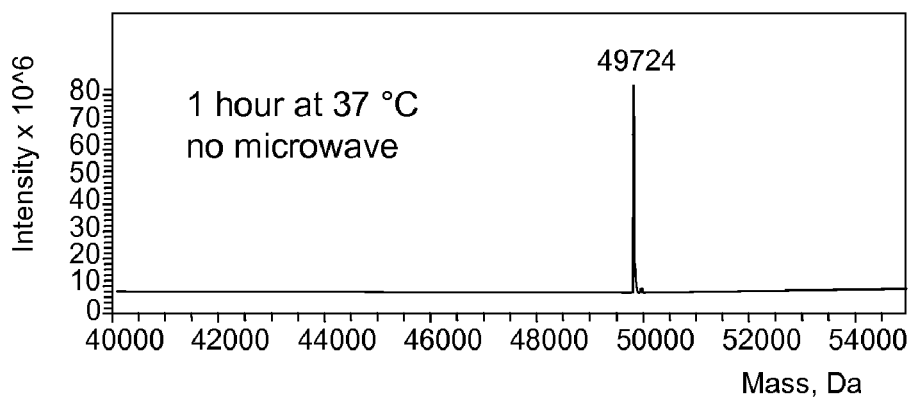
FIG. 4c shows a deconvoluted mass spectra of reduced bevacizumab heavy chain and PNGase F after 60 minutes in a water bath, without microwave irradiation, at 37° C.

Deglycosylation of the heavy chain of reduced antibodies in the microwave also occurred at a considerably faster rate than without microwave irradiation, i.e. in a water bath. FIG. 3a shows the glycosylated heavy chain of bevacizumab (51162 Da [M+H+1445]$^+$). Under microwave irradiation at 37° C. the heavy chain is approximately 75% deglycosylated after 5 minutes (FIG. 3b) and completely deglycosylated (49721 Da [M+H]$^+$) after 10 minutes (FIG. 3c). By contrast, without microwave irradiation at 37° C. the heavy chain is incompletely deglycosylated at 5 minutes (FIG. 4a), only completely deglycosylated sometime between 10 minutes (FIG. 4b) to 60 minutes (FIG. 4c).

Microwave irradiation of antibodies and PNGase F higher temperatures, e.g. at 60° C., was also performed. Although rapid deglycosylation occurred (less than 2 min), significant loss of signal was observed, perhaps indicative of antibody and/or enzyme degradation. For both bevacizumab and trastuzumab, higher temperatures with more frequent time point sampling evidenced deterioration of PNGase F enzyme activity and decrease in overall antibody peak intensity.

Figure 8A:
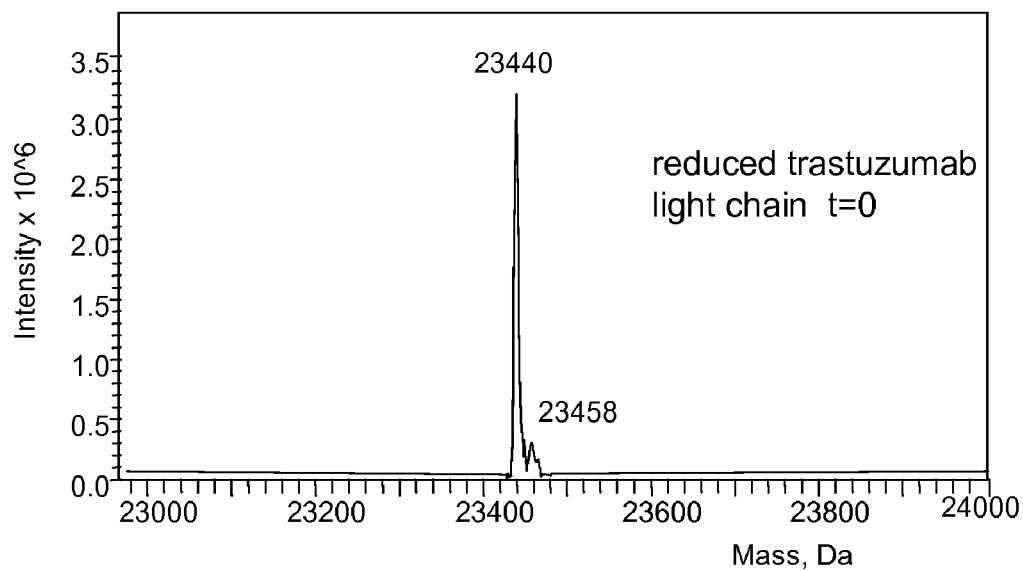
FIG. 8a shows the light chain mass region of a deconvoluted mass spectra of reduced trastuzumab.
Figure 8B:
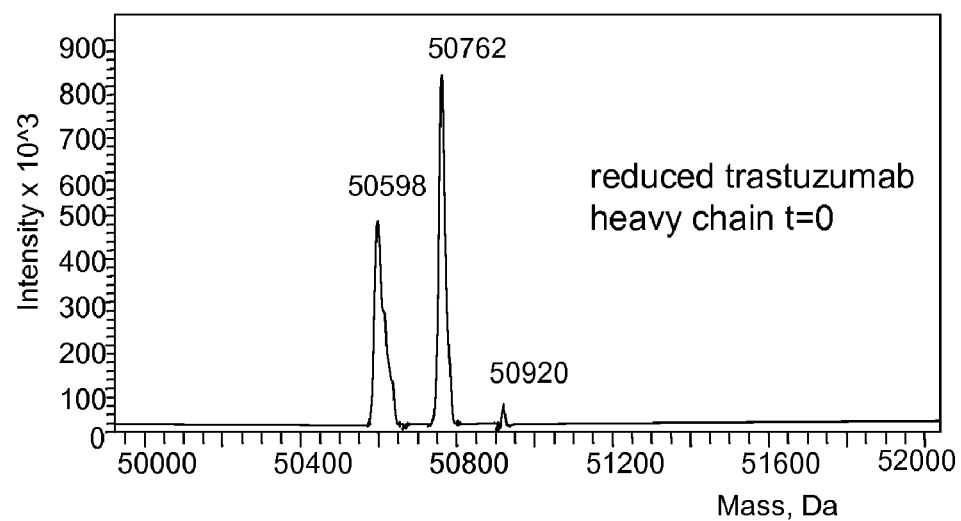
FIG. 8b shows the heavy chain mass region of a deconvoluted mass spectra of reduced trastuzumab.
Figure 9A:
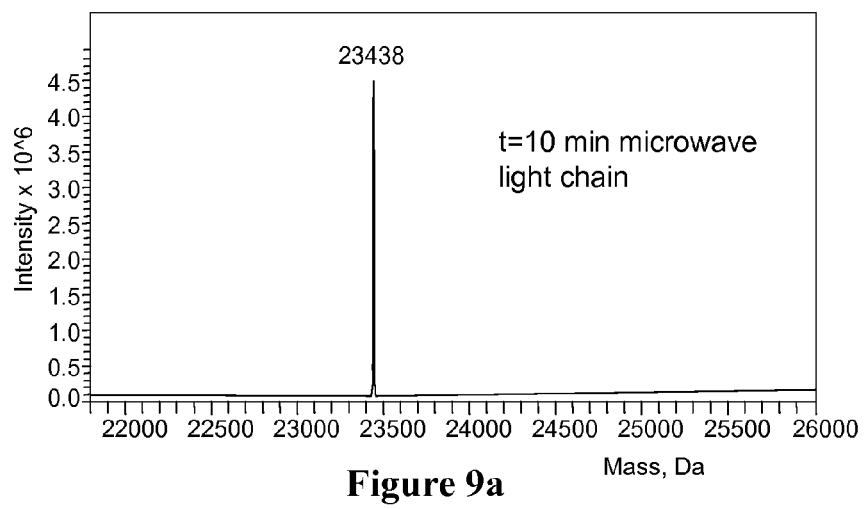
FIG. 9a shows the light chain mass region of a deconvoluted mass spectra of reduced trastuzumab and PNGase F after 10 minutes of microwave irradiation at 45° C.
Figure 9B:
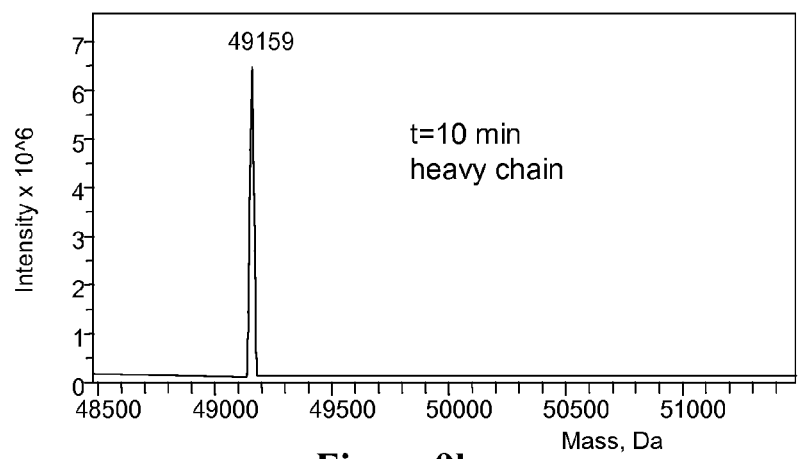
FIG. 9b shows the heavy chain mass region of a deconvoluted mass spectra of reduced trastuzumab and PNGase F after 10 minutes of microwave irradiation at 45° C.

Trastuzumab (HERCEPTIN®, Genentech, South San Francisco, Calif.) was deglycosylated by the microwave conditions of the invention. Trastuzumab exists mainly as the G0 glycoform with a sugar moiety at Asn 297 on the heavy chain. FIGS. 8 and 9 also show the same experiment as bevacizumab, this time analyzing the trastuzumab antibody light (FIGS. 8a and 9a) and heavy chains (FIGS. 8b and 9b). The same observations were made, i.e. that at 60° C., significant losses were incurred, and at the lower temperatures of 37° C. and 45° C., overall protein material was not compromised during the deglycosylation reaction. Again, partial deglycosylation of trastuzumab could be obtained in five minutes, and after 10 minutes deglycosylation was complete. Under the same conditions and without microwave irradiation, complete deglycosylation of trastuzumab requires approximately 12 to 24 hours.

Along with toxin-conjugated antibodies for therapeutic purposes, antibodies may be conjugated with bi-functional chelating agents (BCA) thus enabling radio-imaging to track the distribution of the therapeutic antibodies in animal models. BCAs attach a chelating moiety to a biological targeting vector, in this case an antibody, to incorporate a radioisotope for bio-distribution determination (Gansow O. A. (1991) Int. J. Appl. Instrum. Part B Nucl. Med. Biol. 18:369-382). DOTA (1,4,7,10 tetraazacyclododecane-N,N',N'',N'''-tetraacetic acid) is a well characterized bi-functional conjugation linker that is favored for its ability to produce physiologically stable complexes with trivalent radio-metals. DOTA is a metal-complexing, chelating ligand. DOTA labelling reagents may be reacted with proteins by standard techniques and using reactive functionality of the protein to form a covalent attachment through a stable bond. The DOTA metal complexing linker on the protein complexes certain metal ions through stable ionic bonds. Reactive DOTA labelling reagents are commercially available, such as DOTA-NHS esters. Since a protein typically contains many amines, e.g. lysine side chains, which may react with an active ester labelling reagent, the resulting product is a heterogeneous mixture of proteins with DOTA linkers at various sites on the protein molecule. A distribution of DOTA-labelled proteins may result with zero, one, two, three, and more DOTA groups, and at varying amino acid residues. Due to the heterogeneity of DOTA linkers on an antibody, deconvolution of mass spectra of these antibodies is somewhat more cumbersome than regular "naked" antibody and is often indecipherable. In addition to this, by having one of more glycoforms present in combination with the heterogeneous conjugations, getting an accurate molecular weight of the antibody can be extremely challenging.

Figure 5A:
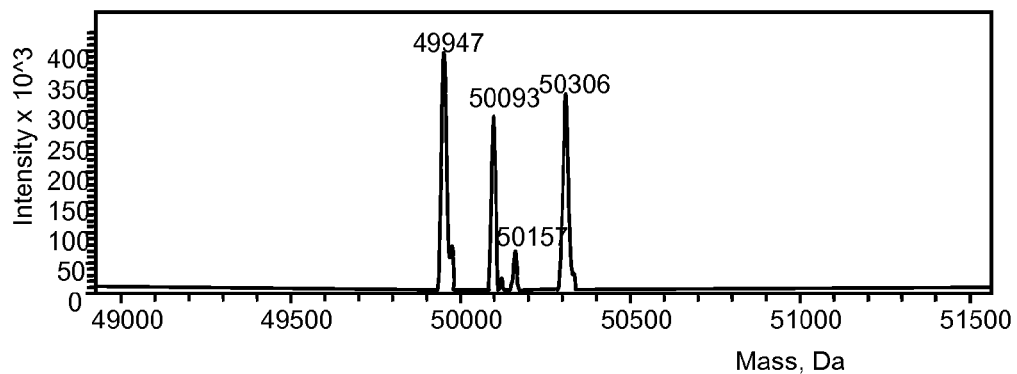
FIG. 5a shows the heavy chain mass region of the deconvoluted mass spectra of reduced, glycosylated anti-CD4.
Figure 5B:
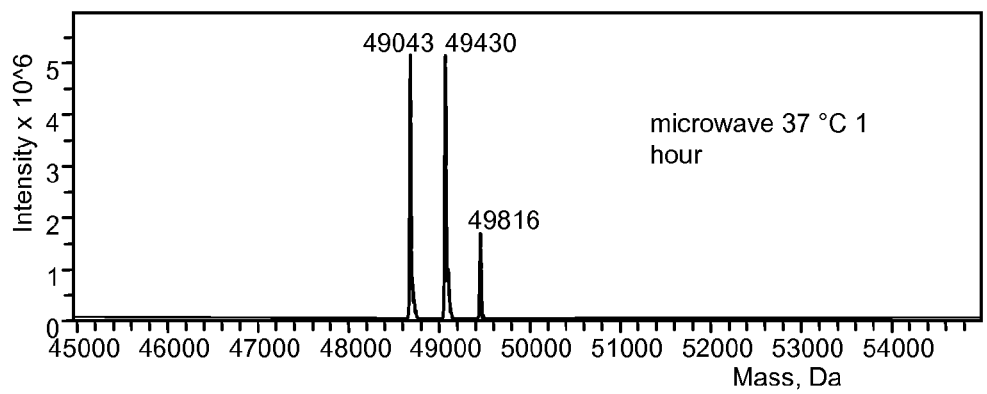
FIG. 5b shows the heavy chain mass region of the deconvoluted mass spectra of reduced anti-CD4-DOTA and PNGase F after 60 minutes of microwave irradiation at 37° C.
Figure 5C:
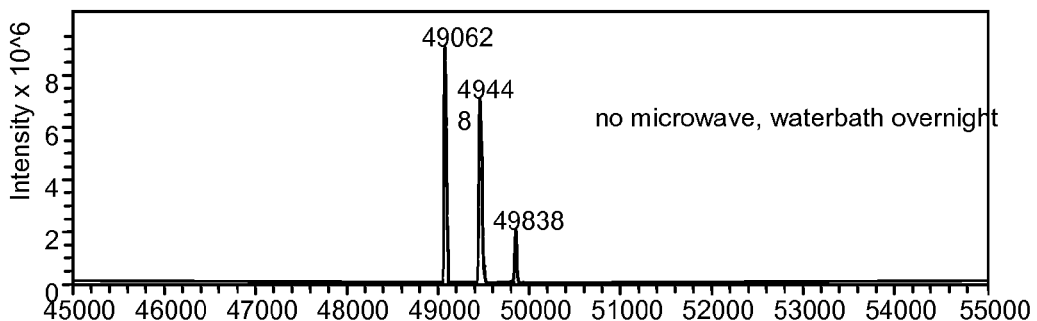
FIG. 5c shows the heavy chain mass region of the deconvoluted mass spectra of reduced anti-CD4-DOTA and PNGase F after overnight in a water bath, without microwave irradiation, at 37° C.

The invention includes microwave assisted deglycosylation methods of DOTA conjugated antibodies. The data from a glycosylated anti-CD4-DOTA conjugate could not be convoluted. FIG. 5a shows the heavy chain mass region of the deconvoluted mass spectra of reduced, glycosylated anti-CD4. FIG. 5b shows the heavy chain mass region of the deconvoluted mass spectra of reduced anti-CD4-DOTA and PNGase F after 60 minutes of microwave irradiation at 37° C. Prior to deglycosylation, the spectrum is too complex to get good deconvolution and therefore an accurate mass could not be determined. By removing the sugar, deconvolution was facilitated and the deglycosylated heavy chain revealed the presence of three variants of DOTA conjugated antibodies seen at masses 49043, 49430, 49816. FIG. 5c shows the heavy chain mass region of the deconvoluted mass spectra of reduced anti-CD4-DOTA and PNGase F after overnight in a water bath, without microwave irradiation, at 37° C. Mass spectrometric identification ascertained that the conjugate was stable during microwave irradiation, time points were again taken using both microwave assisted deglycosylation, and also using the conventional water bath or thermocycler with conventional heating.

Figure 6A:
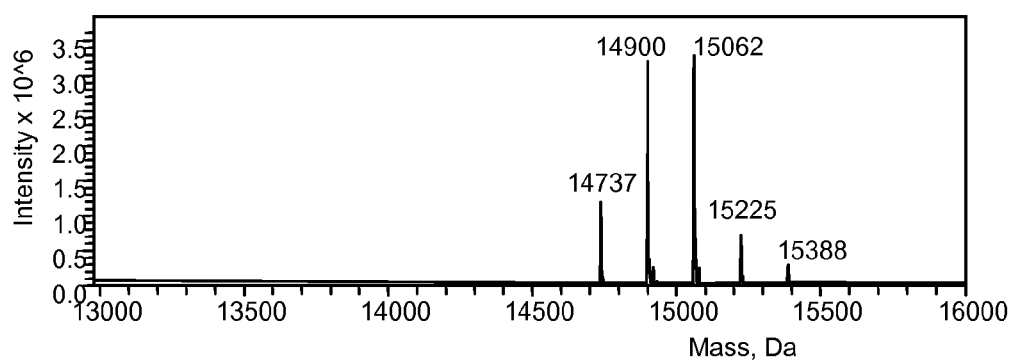
FIG. 6a shows a deconvoluted mass spectra of reduced RNaseB.
Figure 6B:
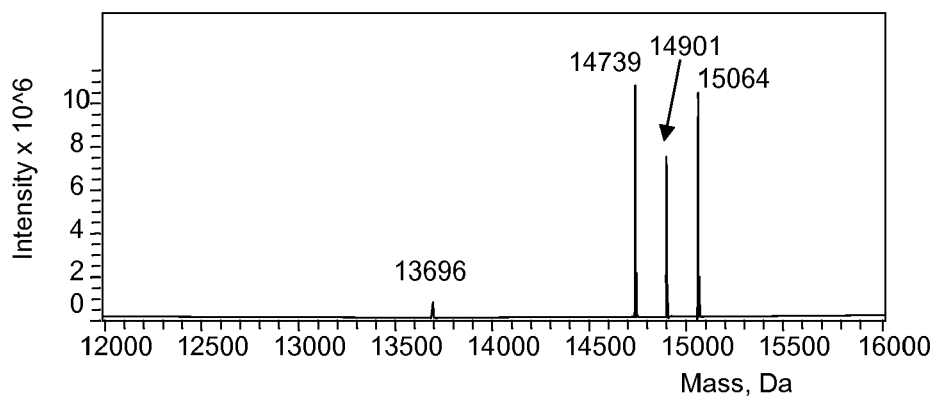
FIG. 6b shows a deconvoluted mass spectra of reduced RNaseB and PNGase F after 5 minutes of microwave irradiation at 40° C.
Figure 6C:
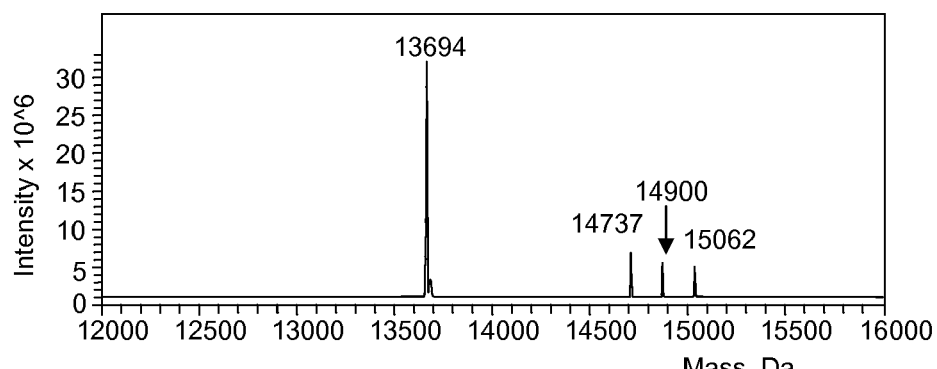
FIG. 6c shows a deconvoluted mass spectra of reduced RNaseB and PNGase F after 10 minutes of microwave irradiation at 40° C.
Figure 6D:
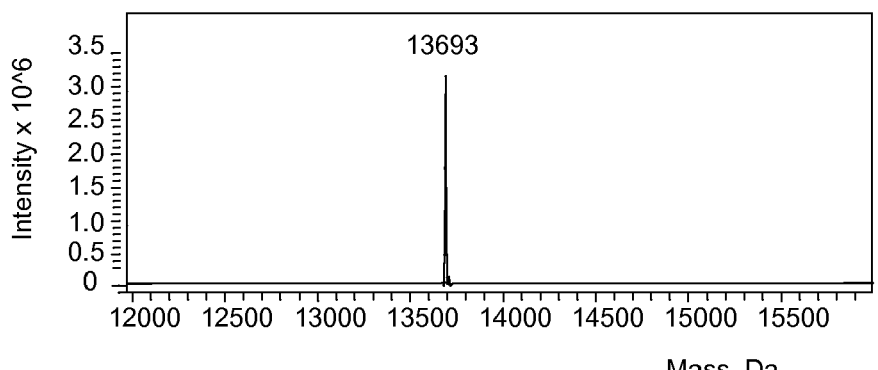
FIG. 6d shows a deconvoluted mass spectra of reduced RNaseB and PNGase F after 60 minutes of microwave irradiation at 40° C.
Figure 7A:
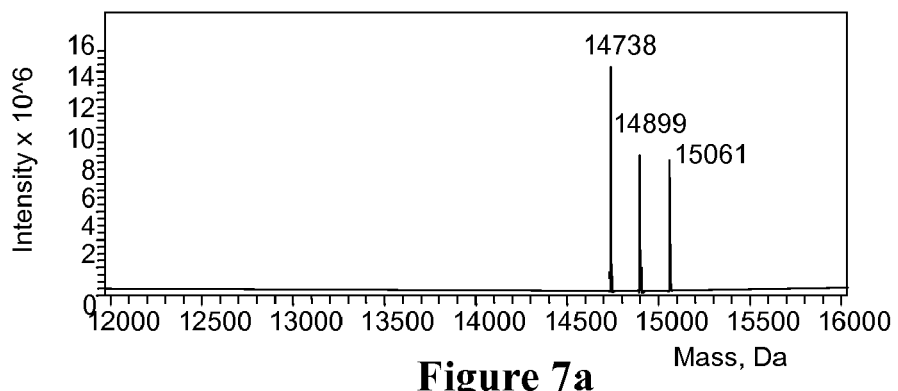
FIG. 7a shows a deconvoluted mass spectra of reduced RNaseB and PNGase F after 5 minutes in a water bath, without microwave irradiation, at 40° C.
Figure 7B:
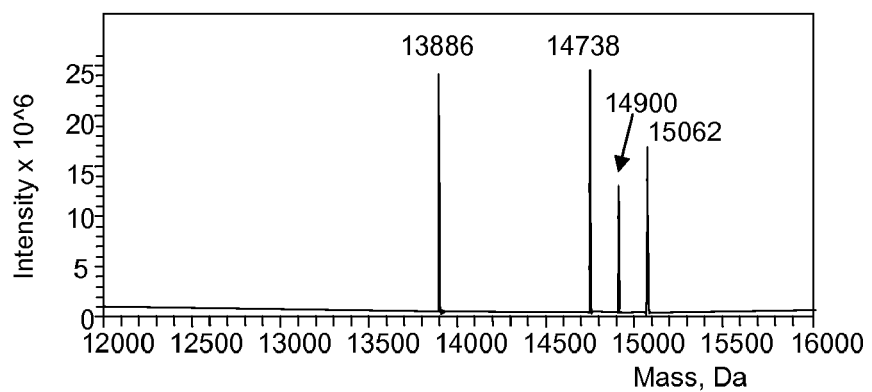
FIG. 7b shows a deconvoluted mass spectra of reduced RNaseB and PNGase F after one hour in a water bath, without microwave irradiation, at 40° C.

The glycoprotein standard RNAse B is a high mannose N-linked oligosaccharide attached via Asn-60. FIG. 6a represents a typical deconvoluted mass spectrum of reduced RNAse B prior to any exposure to PNGase F. Mass spectrometry analysis of deglycosylation of RNAse B with PNGase F with microwave irradiation at 40° C. was conducted at 5 minutes (FIG. 6b), 10 minutes (FIG. 6c), and 60 minutes (FIG. 6d). The same deglycosylation of RNAse B experiment was conducted without microwave irradiation in a water bath at 37° C. for 5 minutes (FIG. 7a), 1 hour (FIG. 7b) and overnight (FIG. 7c) time-points.

Figure 7C:
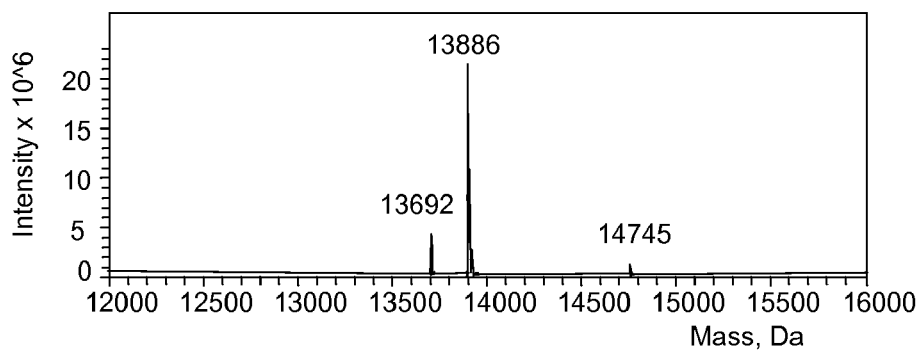
FIG. 7c shows a deconvoluted mass spectra of reduced RNaseB and PNGase F after overnight in a water bath, without microwave irradiation, at 40° C.

Complete deglycosylation of RNAse B after 1 hr in the microwave is observed (FIG. 6d). Compared to the same time point in the water bath (FIG. 7b), deglycosylation occurred at a much faster rate when performed in the presence of microwave energy. Indeed, even after overnight incubation in the water bath at 37° C., complete deglycosylation is not yet observed (FIG. 7c).

When microwave devices are used to conduct the methods of the invention, a useful technique for maximizing their efficiency is to run a plurality of deglycosylation reactions in separate containers ("vessels") at the same time in a single, relatively large resonator. The containers are typically made of a microwave transparent material such as an appropriate plastic, glass, or ceramic. Generally a plurality of two or more containers, and sometimes as many as fifty, are placed in the cavity of a laboratory microwave oven and then radiated with the microwaves. In a typical circumstance, one of the vessels is monitored for pressure, temperature, color change, or some other parameter that measures or indicates the progress of the reaction in that single vessel. The remaining unmonitored vessels may be considered to have behaved identically to the monitored vessel.

Labelled Proteins

The proteins of the invention may be conjugated with any label moiety which can be covalently attached to the protein through a reactive functional group, such as a cysteine thiol or lysine amino (Singh et al (2002) Anal. Biochem. 304:147-15; Harlow E. and Lane, D. (1999) in *Using Antibodies: A Laboratory Manual*, Cold Springs Harbor Laboratory Press, Cold Spring Harbor, N.Y.; Lundblad R. L. (1991) in *Chemical Reagents for Protein Modification*, 2nd ed. CRC Press, Boca Raton, Fla.). The attached label may function to: (i) provide a detectable signal; (ii) interact with a second label to modify the detectable signal provided by the first or second label, e.g. to give FRET (fluorescence resonance energy transfer); (iii) stabilize interactions or increase affinity of binding, with antigen or ligand; (iv) affect mobility, e.g. electrophoretic mobility or cell-permeability, by charge, hydrophobicity, shape, or other physical parameters, or (v) provide a capture moiety, to modulate ligand affinity, antibody/antigen binding, or ionic complexation.

For diagnostic applications, the protein will typically be labeled with a detectable moiety. Numerous labels are available which can be generally grouped into the following categories:

(a) Radioisotopes, such as $^{35}S$, $^{14}C$, $^{125}I$, $^{3}H$, and $^{131}I$. The protein can be labeled with reagents that include a radioisotope or which may complex a radioisotope where the reagent is reactive with the engineered cysteine thiol of the antibody, using the techniques described in *Current Protocols in Immunology*, Volumes 1 and 2, Coligen et al., Ed. Wiley-Interscience, New York, N.Y., Pubs. (1991).

(b) Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the polypeptide variant using the techniques disclosed in *Current Protocols in Immunology*, supra, for example, and fluorescent label reagents from Molecular Probes (Eugene, Oreg.).

(c) Chelating reagents, such as DOTA or crown ethers which may complex metal ions (US 2002/0006379).

(d) Various enzyme-substrate labels are available or disclosed (U.S. Pat. No. 4,275,149). The enzyme generally catalyzes a chemical alteration of the chromogenic substrate that can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRP), alkaline phosphatase (AP), β-galactosidase, glucoamylase, lysozyme, saccharide oxidases (e.g., glucose oxidase, galactose oxidase, and glucose-6-phosphate dehydrogenase), heterocyclic oxidases (such as uricase and xanthene oxidase), lactoperoxidase, microperoxidase, and the like. Techniques for conjugating enzymes to antibodies are described in O'Sullivan et al (1981) "Methods for the Preparation of Enzyme-Antibody Conjugates for use in Enzyme Immunoassay," in *Methods in Enzym.* (ed J. Langone & H. Van Vunakis), Academic Press, New York, 73:147-166.

Examples of enzyme-substrate combinations include, for example:

(i) Horseradish peroxidase (HRP) with hydrogen peroxidase as a substrate, wherein the hydrogen peroxidase oxidizes a dye precursor (e.g., orthophenylene diamine (OPD) or 3,3', 5,5'-tetramethyl benzidine hydrochloride (TMB));

(ii) alkaline phosphatase (AP) with para-nitrophenyl phosphate as chromogenic substrate; and (iii) β-D-galactosidase (β-D-Gal) with a chromogenic substrate (e.g., p-nitrophenyl-β-D-galactosidase) or fluorogenic substrate 4-methylumbelliferyl-β-D-galactosidase.

Numerous other enzyme-substrate combinations are available to those skilled in the art. For a general review of these, see U.S. Pat. No. 4,275,149 and U.S. Pat. No. 4,318,980.

Sometimes, the label is indirectly conjugated with the protein. The protein can be conjugated with biotin and any of the categories of labels mentioned above can be conjugated with avidin, or vice versa. Biotin binds selectively to avidin and thus, the label can be conjugated with the protein in this indirect manner. Alternatively, to achieve indirect conjugation of the label with the protein, the protein is conjugated with a small hapten (e.g., digoxin) and one of the different types of labels mentioned above is conjugated with an anti-hapten protein (e.g., anti-digoxin antibody). Thus, indirect conjugation of the label with the protein can be achieved (Hermanson, G. (1996) in Bioconjugate Techniques Academic Press, San Diego).

Protein and peptide labelling methods are well known. See Haugland (2003) in *Molecular Probes Handbook of Fluorescent Probes and Research Chemicals*, Molecular Probes, Inc.; Brinkley (1992) Bioconjugate Chem. 3:2; Garman (1997) in *Non-Radioactive Labelling: A Practical Approach*, Academic Press, London; Means (1990) Bioconjugate Chem. 1:2; Glazer et al. (1975) in *Chemical Modification of Proteins. Laboratory Techniques in Biochemistry and Molecular Biology* (T. S. Work and E. Work, Eds.) American Elsevier Publishing Co., New York; Lundblad, R. L. and Noyes, C. M. (1984) in *Chemical Reagents for Protein Modification*, Vols. I and II, CRC Press, New York; Pfleiderer, G. (1985) "Chemical Modification of Proteins" in *Modern Methods in Protein Chemistry*, H. Tschesche, Ed., Walter DeGryter, Berlin and New York; and Wong (1991) in *Chemistry of Protein Conjugation and Cross-linking*, CRC Press, Boca Raton, Fla.).

Proteins labelled with two moieties, a fluorescent reporter and quencher in sufficient proximity undergo fluorescence resonance energy transfer (FRET). Reporter groups are typically fluorescent dyes that are excited by light at a certain wavelength and transfer energy to an acceptor, or quencher, group, with the appropriate Stokes shift for emission at maximal brightness. Fluorescent dyes include molecules with extended aromaticity, such as fluorescein and rhodamine, and their derivatives. The fluorescent reporter may be partially or significantly quenched by the quencher moiety in an intact protein. Upon cleavage of the protein by a peptidase or protease, a detectable increase in fluorescence may be measured (Knight, C. (1995) "Fluorimetric Assays of Proteolytic Enzymes", in *Methods in Enzymology*, Academic Press, 248: 18-34).

Labelling reagents typically bear reactive functionality which may react (i) directly with a reactive functional group, e.g. cysteine thiol, of an antibody to form the labelled protein, (ii) with a linker reagent to form a linker label intermediate, or (iii) with a linker antibody to form the labelled antibody. Reactive functionality of labelling reagents include: maleimide, haloacetyl, iodoacetamide succinimidyl ester (e.g. NHS, N-hydroxysuccinimide), isothiocyanate, sulfonyl chloride, 2,6-dichlorotriazinyl, pentafluorophenyl ester, and phosphoramidite, although other functional groups can also be used.

An exemplary reactive functional group is N-hydroxysuccinimidyl ester (NHS) of a carboxyl group substituent of a detectable label, e.g. biotin or a fluorescent dye. The NHS ester of the label may be preformed, isolated, purified, and/or characterized, or it may be formed in situ and reacted with a nucleophilic group of a protein. Typically, the carboxyl form of the label is activated by reacting with some combination of a carbodiimide reagent, e.g. dicyclohexylcarbodiimide, diisopropylcarbodiimide, or a uronium reagent, e.g. TSTU (O—(N-Succinimidyl)-N,N,N',N'-tetramethyluronium tetrafluoroborate, HBTU (O-benzotriazol-1-yl)-N,N,N',N'-tetramethyluronium hexafluorophosphate), or HATU (O-(7-azabenzotriazol-1-yl)-N,N,N',N'-tetramethyluronium hexafluorophosphate), an activator, such as 1-hydroxybenzotriazole (HOBt), and N-hydroxysuccinimide to give the NHS ester of the label. In some cases, the label and the protein may be coupled by in situ activation of the label and reaction with the antibody to form the label-antibody conjugate in one step. Other activating and coupling reagents include TBTU (2-(1H-benzotriazo-1-yl)-1-1,3,3-tetramethyluronium hexafluorophosphate), TFFH(N,N',N'',N'''-tetramethyluronium 2-fluoro-hexafluorophosphate), PyBOP (benzotriazole-1-yl-oxy-tris-pyrrolidino-phosphonium hexafluorophosphate, EEDQ (2-ethoxy-1-ethoxycarbonyl-1,2-dihydroquinoline), DCC (dicyclohexylcarbodiimide); DIPCDI (diisopropylcarbodiimide), MSNT (1-(mesitylene-2-sulfonyl)-3-nitro-1H-1,2,4-triazole, and aryl sulfonyl halides, e.g. triisopropylbenzenesulfonyl chloride.

EXAMPLES

In order to illustrate the invention, the following examples are included. However, it is to be understood that these examples do not limit the invention and are only meant to suggest methods of practicing the invention. Persons skilled in the art will recognize that the exemplary methods, protocols, processes, reagents, and apparatuses described may be readily adapted to practice alternative methods of this invention are deemed to be within the scope of this invention.

Example 1

DOTA Conjugation

The DOTA-NHS-ester was dissolved in dimethylacetamide (DMA, Fluka Chemika, Switzerland) and prepared to concentrations of 60-100 mg/mL. Typical procedures involved buffer exchanging the MAb into PBS with 2 mM EDTA at pH 7.2. Reactions were performed at a ratio of 1 molecule MAb to 4 DOTA molecules (1:4) and carried out at 25° C. while gently stirring on a Thermomixer plate (Eppendorf, Westbury, N.Y.).

Example 2

N-Linked Deglycosylation

In separate experiments, HERCEPTIN® (trastuzumab, Genentech, South San Francisco, Calif.), Avastin® (bevacizumab, Genentech, South San Francisco, Calif.), RNase and the DOTA labeled antibody (10 µg) were each diluted in 0.1 M Tris (MQ water, Millipore Corp, Billerica, Mass.) containing 50 mM dithiothreitol—DTT (Promega, Madison, Wis.) to a final volume of 20 µL. Reduction was allowed to occur for 30 min at room temperature. One unit of PNGase F (Sigma-Aldrich, St. Louis, Mo.) was added to the sample which was either exposed to microwave irradiation using a Discover Microwave instrument (CEM Corp., Newark, Calif.) under varying temperature and time conditions, or for the control, non-microwave assisted experiments, incubated in a water bath. Time-points were taken at intervals from 2 to 60 min at temperatures ranging from 37 to 60° C. using the microwave power settings of 1-20 W. In all cases reactions were stopped immediately with 5% TFA (2 µL) and analyzed directly by mass spectrometry or refrigerated until analysis.

Example 3

Mass Spectrometry Analysis

Intact mass measurements were performed using a Q-TOF mass spectrometer (Micromass, Manchester, UK) or a TSQ Quantum Triple quadrupole mass spectrometer (Thermo Electron, San Jose, Calif.). For analysis by triple quadrupole MS, samples were diluted 1:2 in 0.1% TFA (Solvent A) and 10 µL (approximately 25 pmol) was loaded by auto-sampler onto a PLRP-S 300 A reverse-phase micro-bore column (50× 2.1 mm, Polymer Laboratories, Shropshire, UK). Compounds were separated with a 12 min gradient from 0 to 60% B (Solvent A: 0.05% TFA in water and Solvent B: 0.05% TFA in acetonitrile) and ionized using the electrospray source. Data was collected using Xcalibur™ software (Thermo Electron Corp., Waltham Mass.) and deconvolution was performed using ProMass. Alternatively, 5 µL (25 pmol) of sample was diluted to 40 µL in 0.1% formic acid and passed over a desalting column. Proteins were eluted and ionized using electrospray ionization after which ions were analyzed using the Q-TOF mass spectrometer in full MS mode. Data was interpreted after deconvolution using the MassLynx™ software (Waters Corp., Milford Mass.) to assess the level of deglycosylation.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:

1. A method of deglycosylation of proteins comprising treating an N-linked glycosylated protein with PNGase F enzyme under microwave radiation from 1 to 20 watts power for an hour or less, whereby a deglycosylated protein is formed.

2. The method of claim 1 further comprising the step of applying the deglycosylated protein to a desalting media.

3. The method of claim 2 wherein the deglycosylated protein is eluted from the desalting media in a solution comprising water and an organic solvent.

4. The method of claim 1 further comprising the step of analyzing the deglycosylated protein by mass spectrometry.

5. The method of claim 4 wherein the deglycosylated protein is ionized by electrospray ionization into a mass spectrometer.

6. The method of claim 4 wherein the deglycosylated protein is ionized by MALDI.

7. The method of claim 1 wherein PNGase F is a catalytic amount relative to glycosylated protein.

8. The method of claim 7 wherein the molar ratio of PNGase F to glycosylated protein is between 1:10 to 1:1000.

9. The method of claim 1 wherein the glycosylated protein is a phospho-protein.

10. The method of claim 1 wherein the glycosylated protein is an antibody.

11. The method of claim 10 wherein the antibody is an IgG.

12. The method of claim 11 wherein the antibody is trastuzumab or bevacizumab.

13. The method of claim 11 wherein the IgG is conjugated to a detection label.

14. The method of claim 10 wherein the antibody is conjugated to a metal complexing linker.

15. The method of claim 14 wherein the metal complexing linker is selected from DOTA.

16. The method of claim 10 wherein the antibody is conjugated to a drug moiety.

17. The method of claim 1 further comprising the step of analyzing a sugar moiety removed from the glycosylated protein wherein the sugar moiety is analyzed by mass spectrometry.

18. The method of claim 17 further comprising the step of isolating the sugar moiety by high pH anion-exchange chromatography.

* * * * *

UNITED STATES PATENT AND TRADEMARK OFFICE
CERTIFICATE OF CORRECTION

PATENT NO. : 8,163,518 B2
APPLICATION NO. : 11/741490
DATED : April 24, 2012
INVENTOR(S) : David P. Arnott et al.

Page 1 of 1

It is certified that error appears in the above-identified patent and that said Letters Patent is hereby corrected as shown below:

Title Page, Item (73) should read:

(73) Assignee: ~~Genetech, Inc.,~~ Genentech, Inc., South San Francisco, CA (US)

Signed and Sealed this
Twelfth Day of June, 2012

David J. Kappos
*Director of the United States Patent and Trademark Office*